US008366603B2

(12) United States Patent
Robertson et al.

(10) Patent No.: US 8,366,603 B2
(45) Date of Patent: Feb. 5, 2013

(54) ENDOSCOPE INCLUDING A MULTIFUNCTION CONDUCTOR

(75) Inventors: David W. Robertson, Framingham, MA (US); Victor Shukhat, Canton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1084 days.

(21) Appl. No.: 12/337,064

(22) Filed: Dec. 17, 2008

(65) Prior Publication Data

US 2009/0163769 A1    Jun. 25, 2009

Related U.S. Application Data

(60) Provisional application No. 61/016,020, filed on Dec. 21, 2007.

(51) Int. Cl.
*A61B 1/04* (2006.01)
(52) U.S. Cl. ....................................................... 600/110
(58) Field of Classification Search ........... 600/109–110
See application file for complete search history.

(56) References Cited

U.S. PATENT DOCUMENTS

| 4,920,980 | A | * | 5/1990 | Jackowski ..................... 607/123 |
| 4,930,494 | A | * | 6/1990 | Takehana et al. ............. 600/145 |
| 5,179,935 | A | | 1/1993 | Miyagi |
| 5,348,554 | A | | 9/1994 | Imran et al. |
| 5,439,000 | A | | 8/1995 | Gunderson et al. |
| 5,458,596 | A | | 10/1995 | Lax et al. |
| 5,601,087 | A | | 2/1997 | Gunderson et al. |
| 5,876,326 | A | | 3/1999 | Takamura et al. |
| 6,213,974 | B1 | | 4/2001 | Smith et al. |
| 6,505,066 | B2 | | 1/2003 | Berg et al. |
| 6,960,161 | B2 | | 11/2005 | Amling et al. |
| 7,033,315 | B2 | | 4/2006 | Smith |
| 7,118,584 | B2 | | 10/2006 | Griego et al. |
| 2006/0178562 | A1 | | 8/2006 | Saadat et al. |
| 2007/0185385 | A1 | * | 8/2007 | Noguchi et al. ............. 600/132 |
| 2007/0260119 | A1 | * | 11/2007 | Otawara ....................... 600/129 |
| 2007/0279486 | A1 | * | 12/2007 | Bayer et al. ..................... 348/65 |
| 2008/0171909 | A1 | * | 7/2008 | Onoda et al. ................. 600/118 |
| 2010/0198009 | A1 | | 8/2010 | Farr et al. |

FOREIGN PATENT DOCUMENTS

WO    WO 2004/030526 A    4/2004

OTHER PUBLICATIONS

International Search Report and Written Opinion for PCT/US08/87380, mailed on Mar. 17, 2009; 13 pages.

* cited by examiner

*Primary Examiner* — Clayton E Laballe
*Assistant Examiner* — Dennis Hancock
(74) *Attorney, Agent, or Firm* — Bookoff McAndrews, PLLC

(57) ABSTRACT

In one embodiment, an endoscope includes an elongate member having a proximal end portion and a distal end portion. The distal end portion is configured to be inserted into a body lumen. An electrical component is disposed within the distal end portion of the elongate member and configured to produce a signal. An elongate conductive mechanical component has a proximal end portion and a distal and portion. The distal end portion of the elongate conductive mechanical component is electrically coupled to the electrical component and configured to conduct the signal or electrical power from/to the electrical component to/from the proximal end portion of the elongate conductive mechanical component.

20 Claims, 9 Drawing Sheets

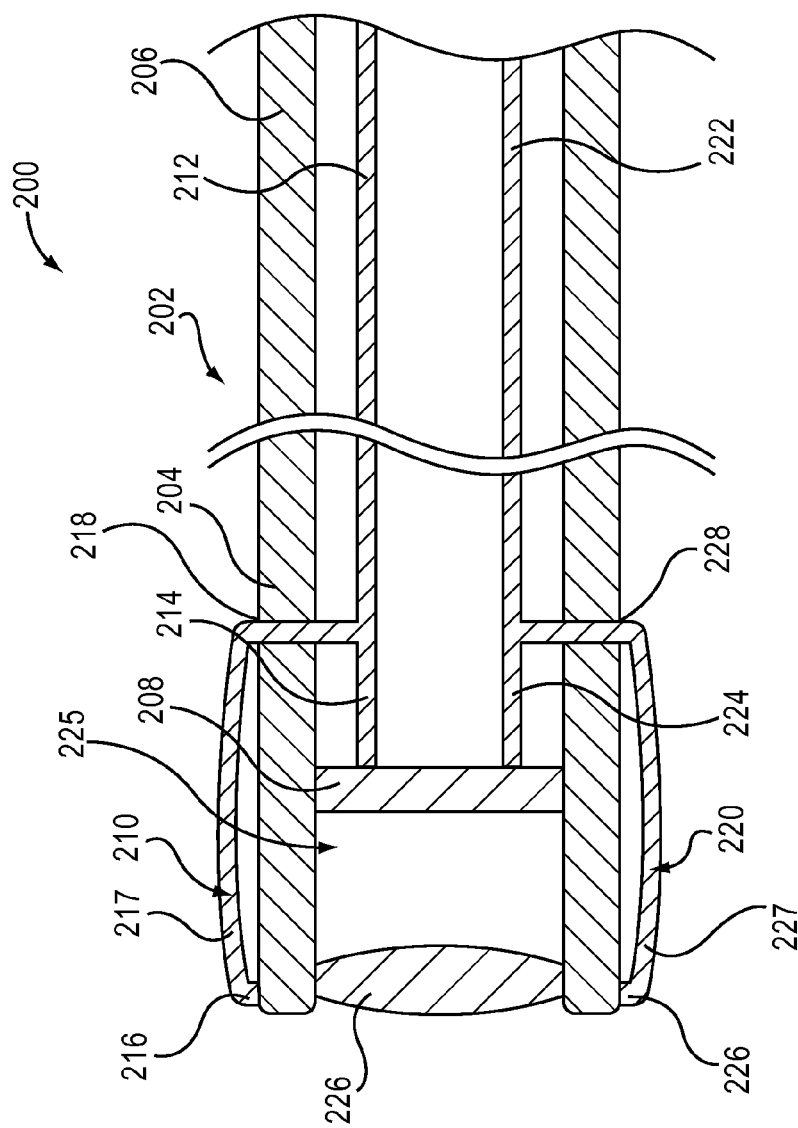
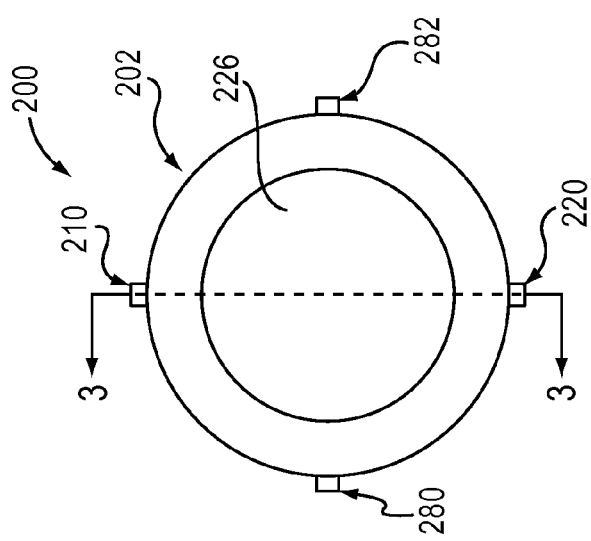
FIG.3
FIG.2

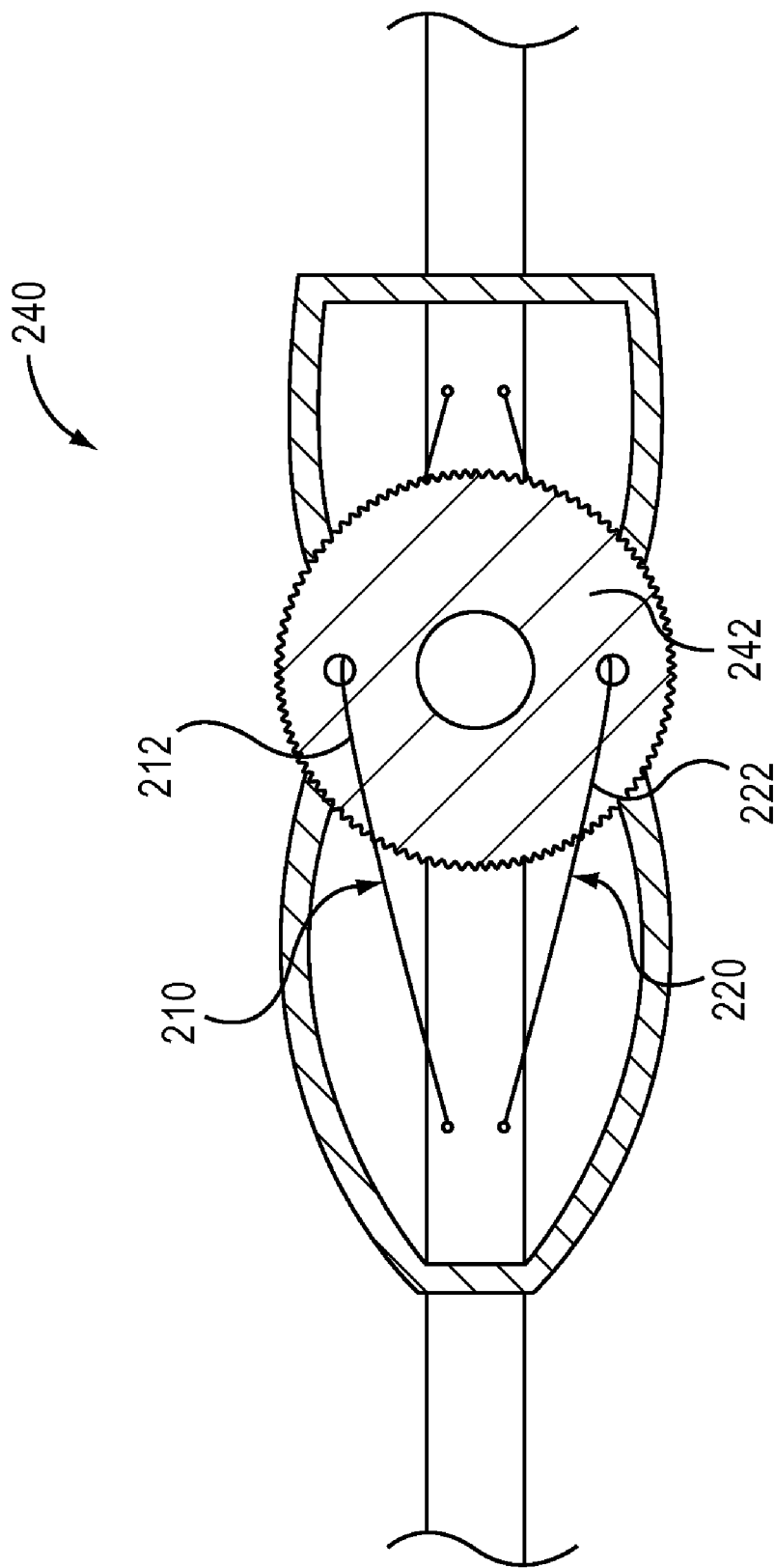

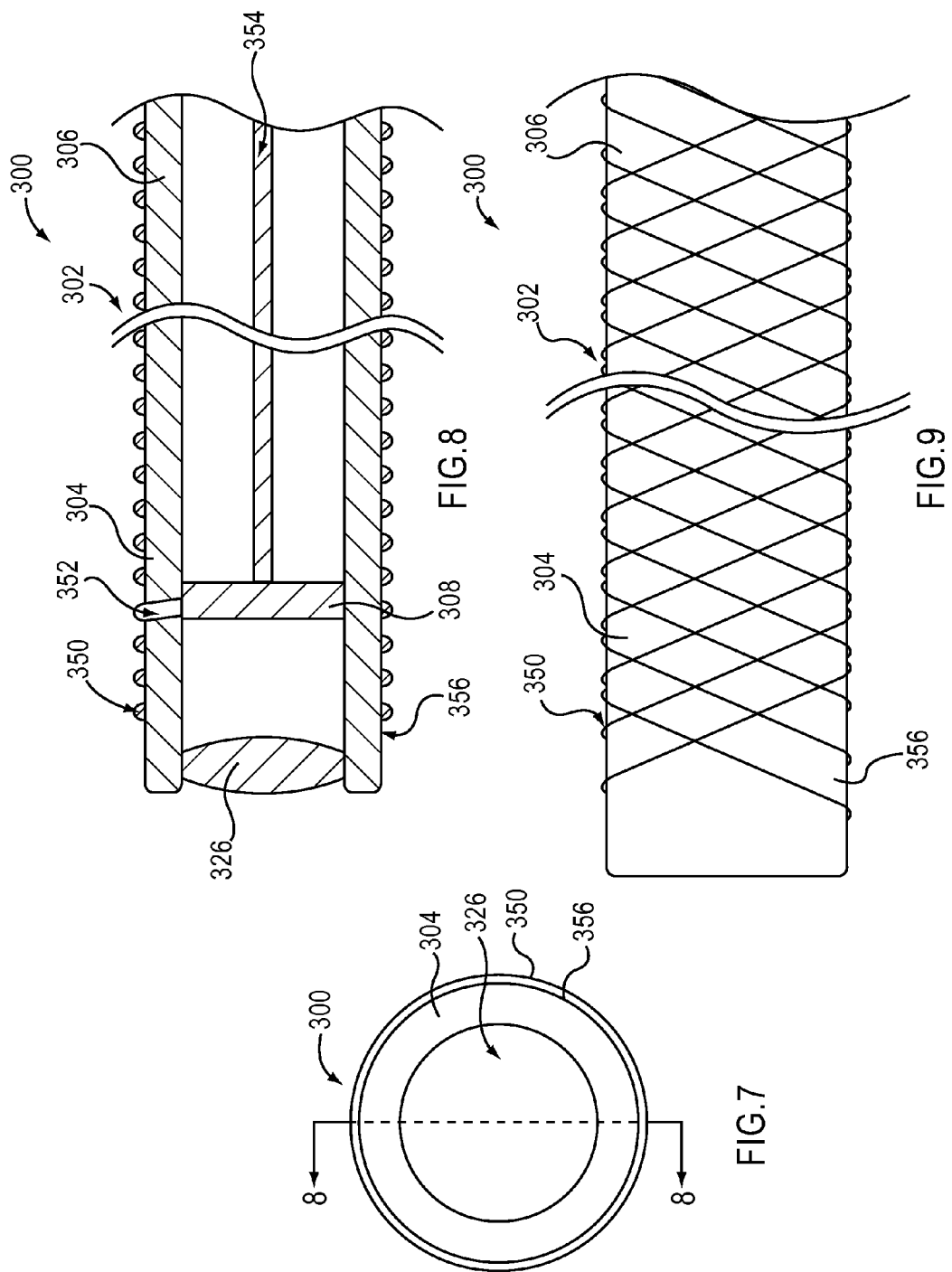

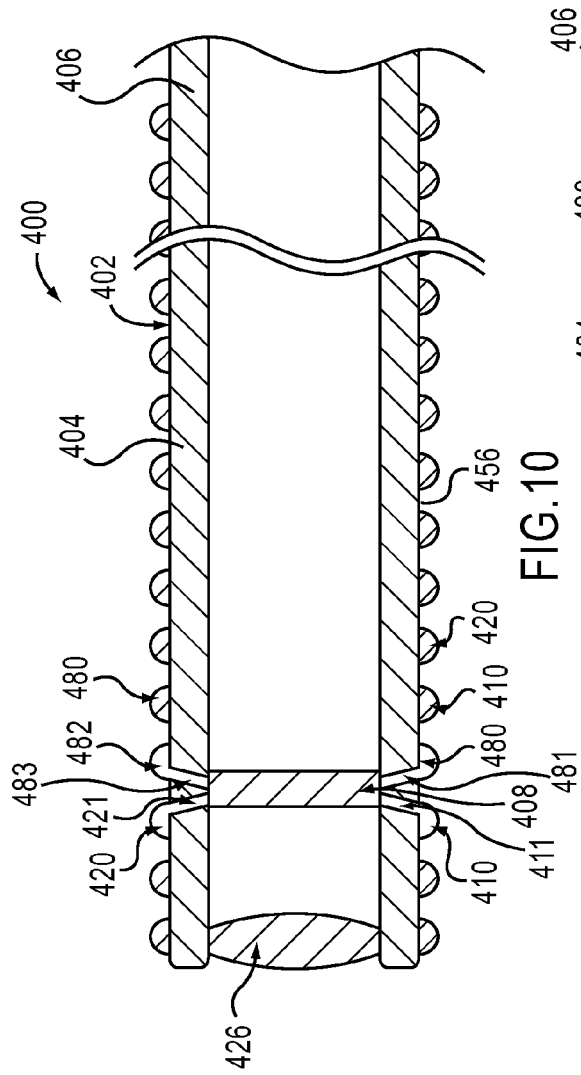
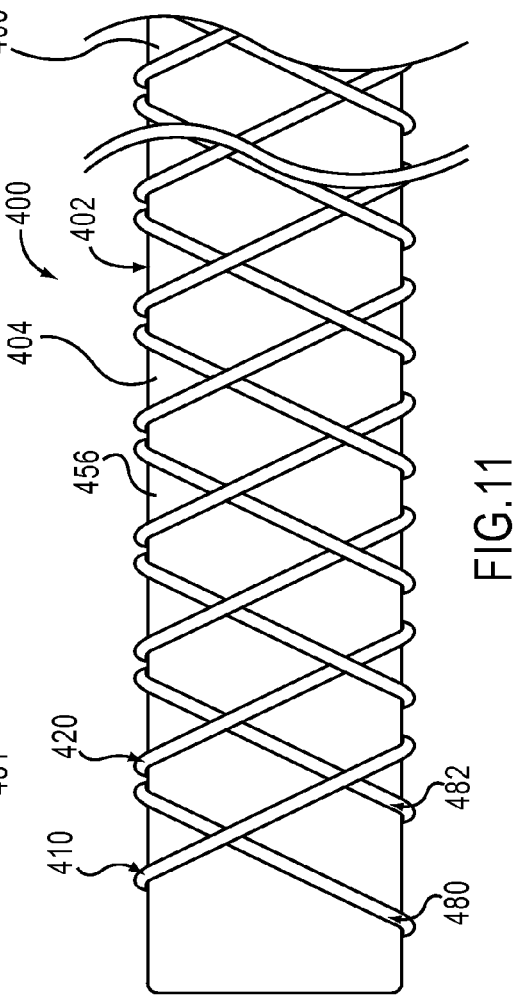

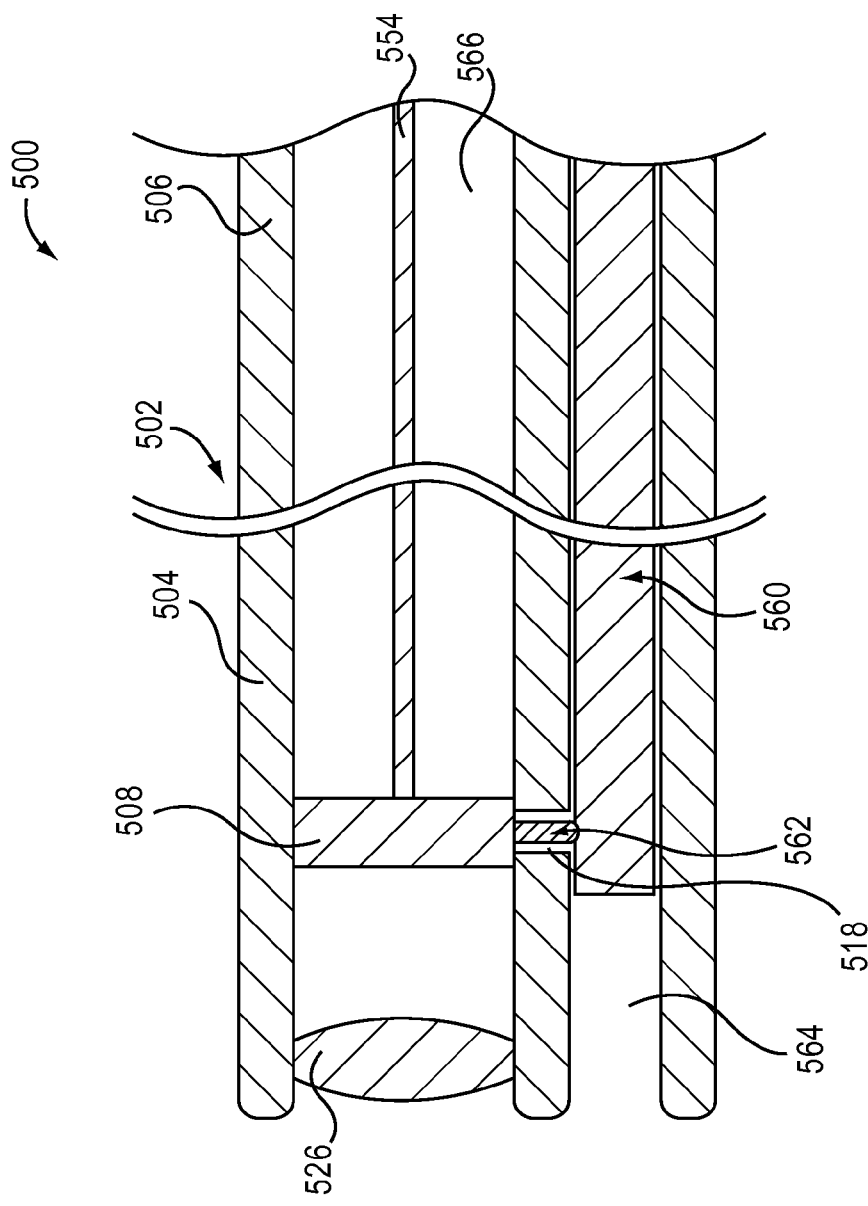
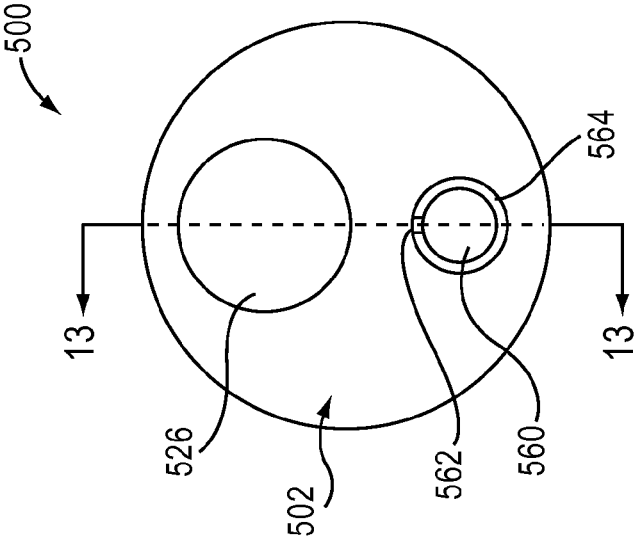
FIG. 13
FIG. 12

ENDOSCOPE INCLUDING A MULTIFUNCTION CONDUCTOR

CROSS-REFERENCE TO RELATED APPLICATIONS

This application claims priority to U.S. Provisional Patent Application Ser. No. 61/016,020, entitled "Endoscope Including a Multifunction Conductor," filed Dec. 21, 2007, the disclosure of which is hereby incorporated by reference in its entirety.

BACKGROUND

This invention relates to a medical device and more particularly to an endoscope having a conductive mechanical component that can perform a mechanical function and also conduct an electrical signal and/or electrical power.

Endoscopes have applications in a wide variety of medical procedures. For example, one such procedure is directed to insertion of an endoscope into a body lumen of a patient to obtain images of a gastrointestinal system. A variety of different types of endoscopes have various functionality. For example, some endoscopes can be used to image body lumens and some endoscopes can be used to view a body lumen. Some endoscopes that provide multiple functions can often require multiple components that are each related to a different function from a set of multiple functions. Such endoscopes can be large (e.g., large outer diameter) preventing use in some applications. For example, some body lumens, such as a ureter, can only receive a very small diameter endoscope.

A need exists for an endoscope having one or more components that can perform multiple functions, reducing the number of components needed to operate the endoscope.

SUMMARY OF THE INVENTION

In one embodiment, an endoscope includes an elongate member having a proximal end portion and a distal end portion. The distal end portion is configured to be inserted into a body lumen. An electrical component is disposed within the distal end portion of the elongate member and configured to produce a signal. An elongate conductive mechanical component has a proximal end portion and a distal and portion. The distal end portion of the elongate conductive mechanical component is electrically coupled to the electrical component and configured to conduct the signal from the electrical component to the proximal end portion of the elongate conductive mechanical component.

BRIEF DESCRIPTION OF THE DRAWINGS

FIG. 2 is a distal end view of a medical device according to an embodiment of the invention.

FIG. 3 is a cross-sectional view of a portion of the medical device of FIG. 2 taken along line 3-3 in FIG. 2.

FIG. 4 is a partial cross-sectional view of a portion of the medical device of FIG. 2.

FIG. 7 is a distal end view of a medical device according to an embodiment of the invention.

FIG. 8 is a cross-sectional view of a portion of the medical device of FIG. 7 taken along line 8-8 in FIG. 7.

FIG. 9 is a side view of a portion of the medical device of FIG. 7.

FIG. 10 is a cross-sectional view of a medical device according to another embodiment of the invention.

FIG. 11 is a side view of the medical device of FIG. 10.

FIG. 12 is a distal end view of a medical device according to another embodiment of the invention.

FIG. 13 is a cross-sectional view of a portion of the medical device of FIG. 12 taken along line 13-13 in FIG. 12.

DETAILED DESCRIPTION

Figure 1:
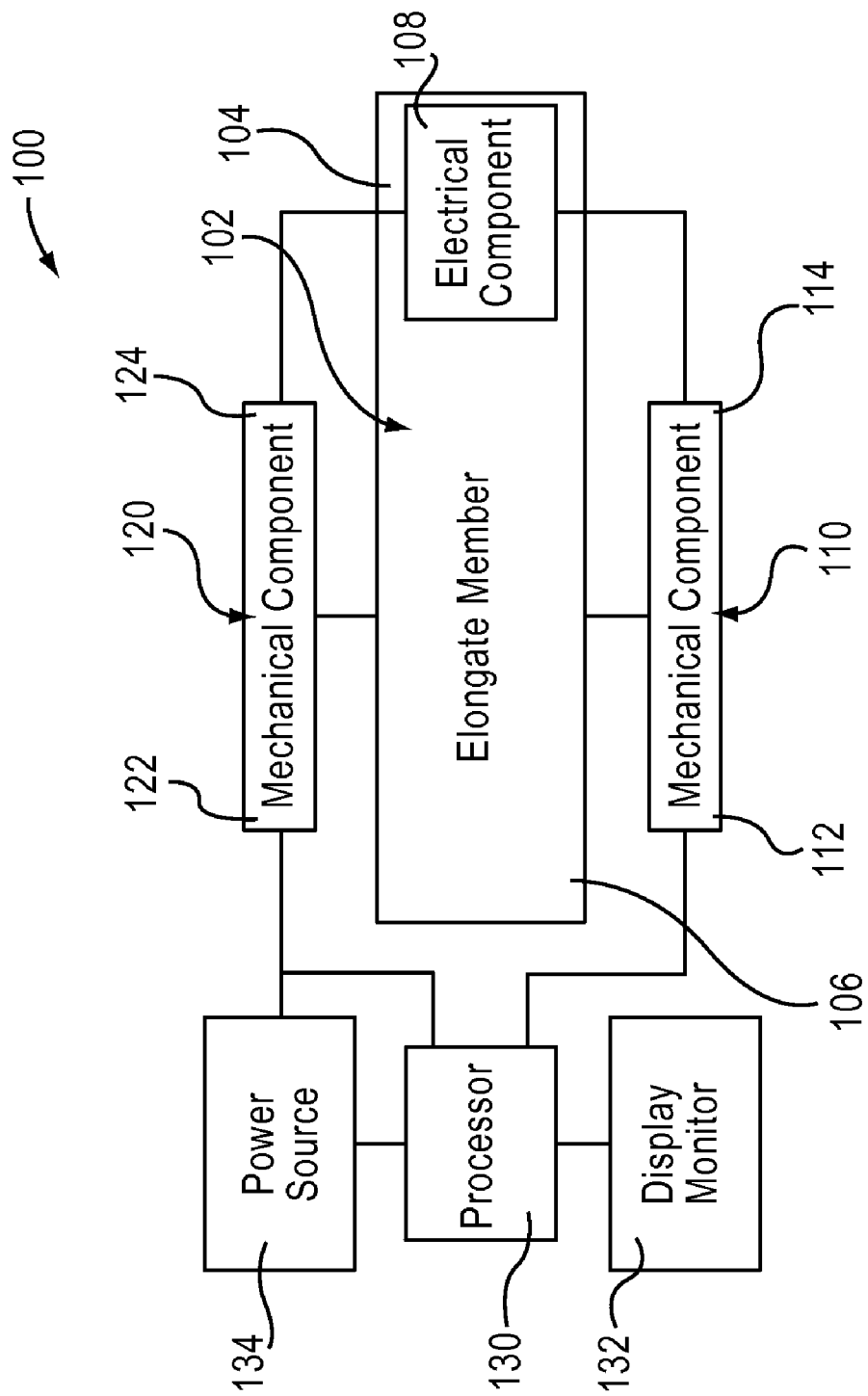
FIG. 1 is a schematic illustration of a medical device according to an embodiment of the invention.

The medical devices described herein can be used in a variety of different body lumens of a patient, such as, for example, a gastrointestinal lumen, a vascular lumen, a ureteral lumen, etc. As described herein, a medical device can include an electrical component disposed at a distal end portion of the medical device that can generate an electrical signal. The electrical component can be, for example, an imaging device, such as a charge coupled device (CCD), a pressure sensor, or a temperature sensor. For example, in some embodiments, the electrical signal can be an imaging signal. The electrical signal can then be conducted to a proximal end portion of the medical device to, for example, a processor or display monitor. The electrical signal can be conducted to the proximal end of the medical device using a component of the medical device that also provides a mechanical function. For example, a conductive mechanical component coupled to the electrical component can be used to perform a mechanical function and an electrical function such as conducting electrical power to the electrical component or conducting a signal produced by the electrical component.

Using a conductive mechanical component to serve as the electrical transmission medium for an electrical component can reduce the number of components of the medical device, and thus can also reduce the size of the medical device. For example, in some embodiments, a medical device (also referred to herein as an endoscope) can include an imaging device (e.g., a CCD) at a distal end portion of the endoscope, and a steering component electrically coupled (e.g., conductively) to the imaging device. The steering component can be used to mechanically maneuver the endoscope within a body lumen and can also serve as the transmission medium for an imaging signal generated by the imaging device.

In one embodiment, an endoscope includes an elongate member having a proximal end portion and a distal end portion. The distal end portion is configured to be inserted into a body lumen. An electrical component is disposed within the distal end portion of the elongate member and configured to produce a signal. An elongate conductive mechanical component has a proximal end portion and a distal and portion. The distal end portion of the elongate conductive mechanical component is electrically coupled to the electrical component and configured to conduct the signal from the electrical component to the proximal end portion of the elongate conductive mechanical component or to conduct power from the proximal end portion of the elongate conductive mechanical component to the electrical component.

In another embodiment, an endoscope includes an elongate member having a proximal end portion and a distal end portion. The distal end portion is associated with a diameter of a body lumen. The elongate member has a first configuration and a second configuration different than the first configuration. An electrical component is coupled to a distal end portion of the elongate member. A steering component is electrically coupled to the electrical component and coupled to the distal end portion of the elongate member. The steering component is configured to conduct a signal from the electrical component to the proximal end portion of the elongate member. The steering component is configured to move the elongate member from the first configuration to the second configuration.

The terms "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the endoscope end inserted inside a patient's body would be the distal end of the endoscope, while the endoscope end outside a patient's body would be the proximal end of the endoscope.

FIG. 1 is a schematic illustration of a medical device according to an embodiment of the invention. A medical device 100 (also referred herein as an "endoscope") includes an elongate member 102 having a proximal end portion 106 and a distal end portion 104. The distal end portion 104 can be inserted at least partially into a body lumen of a patient. An electrical component 108, such as an imaging device, or a pressure or temperature sensor, can be coupled to the distal end portion 104 of the elongate member 102. For example, an electrical component 108 can be disposed within a lumen (not shown) of the distal end portion 104 of the elongate member 102. The electrical component 108 can produce an electrical signal, such as, for example, an imaging signal, or a signal indicating a pressure or a temperature measured at or proximate to the distal end portion 104 of the elongate member 102.

A first elongate conductive mechanical component 110 has a proximal end portion 112 and a distal end portion 114. The distal end portion 114 of the first elongate conductive mechanical component 110 is electrically coupled to the electrical component 108. The first elongate conductive mechanical component 110 can perform a mechanical function of the endoscope 100 and also be used to conduct a signal from the electrical component 108 to the proximal end portion 112 of the first elongate conductive mechanical component 110. For example, the first elongate conductive mechanical component 110 can be a steering component, such as a steering wire, used to maneuver the distal end portion 104 of the elongate member 102. The first elongate conductive mechanical component 110 can alternatively be a braided wire disposed around the elongate member 102 and used to provide structural support to the elongate member 102. Thus, the first elongate conductive mechanical component 110 can be a variety of different configurations and used to perform a variety of different mechanical functions while also providing the transmission means for an electrical signal (or electrical power) generated by or conducted to the electrical component 108.

The proximal end portion 112 of the first elongate conductive mechanical component 110 can be operatively coupled to, for example, a processor 130. The processor 130 can be coupled to a display monitor 132, which can display an image produced by an imaging device as described above. In some embodiments, the proximal end portion 112 of the first elongate conductive mechanical component 110 can also, or optionally, be electrically coupled to a processor 130 configured to receive, manipulate, process and/or conduct the signal to another device, such as the display monitor 132.

The endoscope 100 can optionally include a second elongate conductive mechanical component 120 having a proximal end portion 122 and a distal end portion 124. The second elongate conductive mechanical component 120 can have the same or different configuration as the first elongate conductive mechanical component 110. The proximal end portion 122 of the second elongate conductive mechanical component 120 can be electrically coupled to a power source 134. The distal end portion 124 of the second elongate conductive mechanical component 120 can be electrically coupled to the electrical component 108. As with the first elongate conductive mechanical component 110, the second elongate conductive mechanical component 120 can perform a mechanical function and also be used to perform an electrical function of the endoscope 100. For example, the second elongate conductive mechanical component 120 can be, a steering component, such as a steering wire, used together with the first elongate conductive mechanical component 110 to maneuver the distal end portion 104 of the elongate member 102 within a body lumen. The electrical function of the second elongate conductive mechanical component 120 can be, for example, to conduct electrical power from the power source 134 to the electrical component 108 via the second elongate conductive mechanical component 120. In some embodiments, the second elongate conductive mechanical component 120 can be used for other functions, for example, to conduct heat to or remove heat from the distal end portion of the endoscope 100.

In one example, use of the endoscope 100, the elongate member 102 can be maneuvered within a body lumen of a patient using the first elongate conductive mechanical component 110 and/or the second elongate conductive mechanical component 120 as steering components. In such an embodiment, the elongate member 102 can be moved between a substantially straight configuration and a curved configuration while disposed within a body lumen. The first and second elongate conductive mechanical components 110 and 120 can be selectively actuated via an actuator or control device (not shown) coupled to the first and second elongate conductive mechanical components 110 and 120 as described in more detail below with specific reference to specific embodiments. As the first elongate conductive mechanical component 110 and/or the second elongate conductive mechanical component 120 are actuated, the distal end portion 104 of the elongate member 102 will move or bend in response to the actuation.

In some embodiments, the second elongate conductive mechanical component 120 can alternatively be used, for example, to conduct a second signal from the electrical component 108 to the proximal end portion 122 of the second elongate conductive mechanical component 120. In yet another alternative embodiment, the second elongate conductive mechanical component 120 can be used to receive a second signal from the electrical component 108 at the proximal end portion 122 of the second elongate conductive mechanical component 120. The proximal end portion 122 of the second elongate conductive mechanical component 120 can also, or optionally be electrically coupled to the processor 130 and/or display monitor 132.

In an alternative embodiment, the electrical functionalities of the first and second elongate conductive mechanical components 110 and 120 can be reversed. For example, the electrical function of the second elongate conductive mechanical component 120 can be to conduct a signal produced by the endoscopic imager 308 to the proximal end portion 306 of the elongate member 302. The electrical functionality of the first elongate conductive mechanical component 110 can be to conduct electrical power from the proximal end portion 306 of the elongate member 302 to the endoscopic imager 308.

In some embodiments, the endoscope 100 can include a second electrical component (not shown) coupled to the distal end portion 104 of the elongate member 102. The second electrical component can be, for example, an endoscopic imager, a thermal sensor, a pressure sensor, a detector, or the like. An example of such an endoscope is described below with reference to FIG. 8.

FIGS. 2-6 illustrate a medical device according to an embodiment of the invention. As shown in FIGS. 2 and 3, an endoscope 200 includes an elongate member 202 having a distal end portion 204 and a proximal end portion 206. An electrical component 208 is disposed within the distal end portion 204 of the elongate member 202. The electrical component 208 in this embodiment is an imaging device (e.g., CCD). In other embodiments, the electrical component can be, a CMOS imager, a thermal sensor, a pressure sensor, a temperature sensor, etc. The proximal end portion 206 of the elongate member 202 can be operatively coupled to a visual display (not shown) and/or a processor (not shown).

The endoscope 200 includes a first steering component 210, a second steering component 220, a third steering component 280 and a fourth steering component 282. The steering components 210, 220, 280 and 282 each have a mechanical function and an electrical function. The steering components 210, 220, 280 and 282 can each be, for example, steering wires or cables. The first steering component 210 has a proximal end portion 212 and a first distal end portion 214. The first distal end portion 214 of the first steering component 210 is electrically coupled to the electrical component 208. The proximal end portion 212 of the first steering component 210 can be coupled to, for example, the visual display and/or processor. The first steering component 210 can be used to conduct a signal generated by the electrical component 208 to the proximal end portion 212 of the first steering component 210. In some embodiments, the first steering component 210 can conduct the signal from the electrical component 208 to the visual display and/or processor coupled to the proximal end portion 212 of the first steering component 210. For example, an image associated with the image signal can be displayed on the display monitor.

Similarly, the second steering component 220 has a proximal end portion 222 and a first distal end portion 224. The first distal end portion 224 of the second steering component 220 is electrically coupled to the electrical component 208. The proximal end portion 222 of the second steering component 220 can be coupled to a power source (not shown). The second steering component 220 can be used as a transmission medium to conduct electrical power from the power source to the electrical component 208.

Similarly, the third steering component 280 and the fourth steering component 282 each have a proximal end portion (not shown) and a first distal end portion (not shown). The first distal end portions of both the third steering component 280 and the fourth steering component 280 are electrically coupled to the electrical component 208. The proximal end portion of the third steering component 280 can be coupled to, for example, the visual display and/or processor. The third steering component 280 can be used as a transmission medium to conduct a signal generated by the electrical component 208 to the proximal end portion of the third steering component 280. The proximal end portion of the fourth steering component 282 can be coupled to the power source. The fourth steering component 282 can be used as a transmission medium to conduct electrical power from the power source to the electrical component 208.

In this embodiment, the first steering component 210 and the third steering component 280 conduct different signals (e.g., S+ and S−, respectively) from the electrical component 208 to the visual display and/or processor. The second steering component 220 and the fourth steering component 282 conduct collectively electrical power (e.g., P+ and P−, respectively) from the power source to the electrical component 208. In one embodiment, the first and third steering components can conduct the same signal from the electrical component 208 to the visual display and/or processor. In another embodiment, the first steering component can conduct electrical power from the power source to the electrical component. In such an embodiment, the second, third and fourth steering components can conduct a signal from the electrical component to the visual display and/or processor.

Returning to the embodiment shown in FIGS. 2-6, the first steering component 210 is disposed, in part, within a lumen 225 of the elongate member 202 as shown in FIG. 3. A second distal end portion 217 of the first steering component 210 is disposed through a first aperture 218 of the elongate member 202 and along a portion of an outer surface of the elongate member 202. As shown in FIGS. 2 and 3, a distal end 216 of the second distal end portion 217 is coupled to the distal end portion 204 of the elongate member 202. Similarly, the second steering component 220 is disposed, in part, within the lumen 225 of the elongate member 202. A second distal end portion 227 of the second steering component 220 is disposed through a second aperture 228 of the elongate member 202 and along a portion of the outer surface of the elongate member 202. A distal end 226 of the second distal end portion 227 is coupled to the distal end portion 204 of the elongate member 202. In some embodiments, the first steering component 210 and the second steering component 220 are each hermetically sealed to the respective aperture 218 and 228, to inhibit fluids outside the endoscope 200 from entering into the lumen 225 of the elongate member 202. In some embodiments, the first, second, third and fourth steering components 210, 220, 280 and/or 282 can include an insulation layer (i.e., an electrically-insulative layer).

In the illustrated embodiment, the third steering component 280 is disposed, in part, within the lumen 225 of the elongate member 202. A second distal end portion (not shown) of the third steering component 280 is disposed through a third aperture (not shown) of the elongate member 202 and along a portion of the outer surface of the elongate member 202. A distal end (not shown) of the second distal end portion of the third steering component 280 is coupled to the distal end portion 204 of the elongate member 202. Similarly, the fourth steering component 282 is disposed, in part, within the lumen 225 of the elongate member 202. A second distal end portion 284 of the fourth steering component 282 is disposed through a fourth aperture (not shown) of the elongate member and along a portion of the outer surface of the elongate member 202. A distal end 286 of the second distal end portion 284 is coupled to the distal end portion 204 of the elongate member 202. In some embodiments, the third steering component 280 and the fourth steering component 282 are each hermetically sealed to the respective aperture, to inhibit fluids outside the endoscope 200 from entering into the lumen 225 of the elongate member 202.

In the illustrated embodiment, the second distal end portion of the third steering component 280 is positioned such that a distance between the second distal end portion of the third steering component 280 and the second distal end portion 217 of the first steering component 210 is substantially equal to a distance between the second distal end portion of the third steering component 280 and the second distal end portion 227 of the second steering component 220. The second distal end portion 284 of the fourth steering component 282 is positioned such that a distance between the second distal end portion 284 of the fourth steering component 282 and the second distal end portion 217 of the first steering component 210 is substantially equal to a distance between the second distal end portion 284 of the fourth steering component 282 and the second distal end portion 227 of the second steering component 220.

Figure 5:
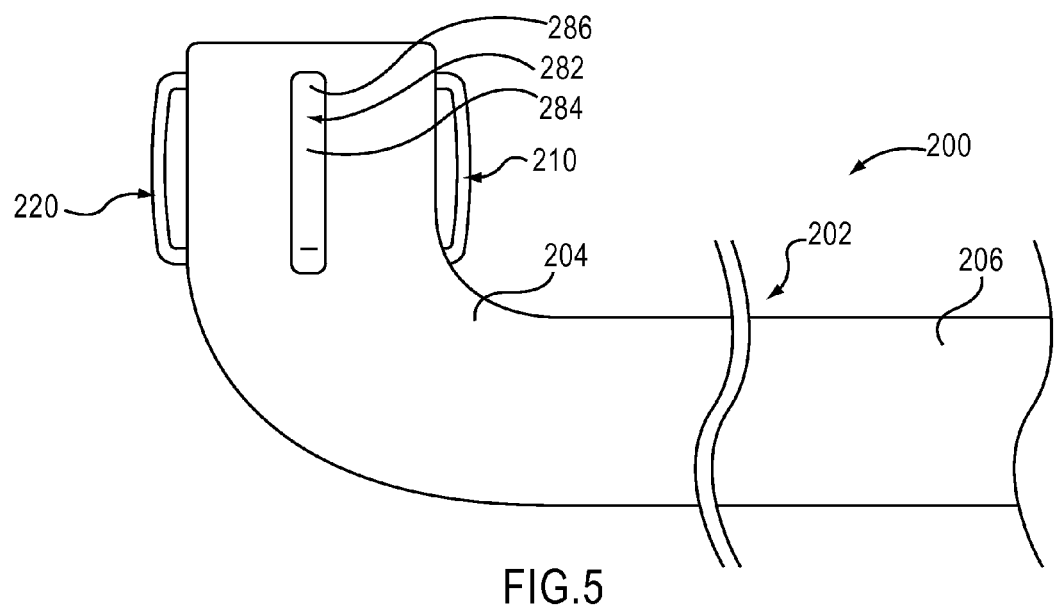
FIGS. 5 and 6 are each a side view of a portion of the medical device of FIG. 2.
Figure 6:
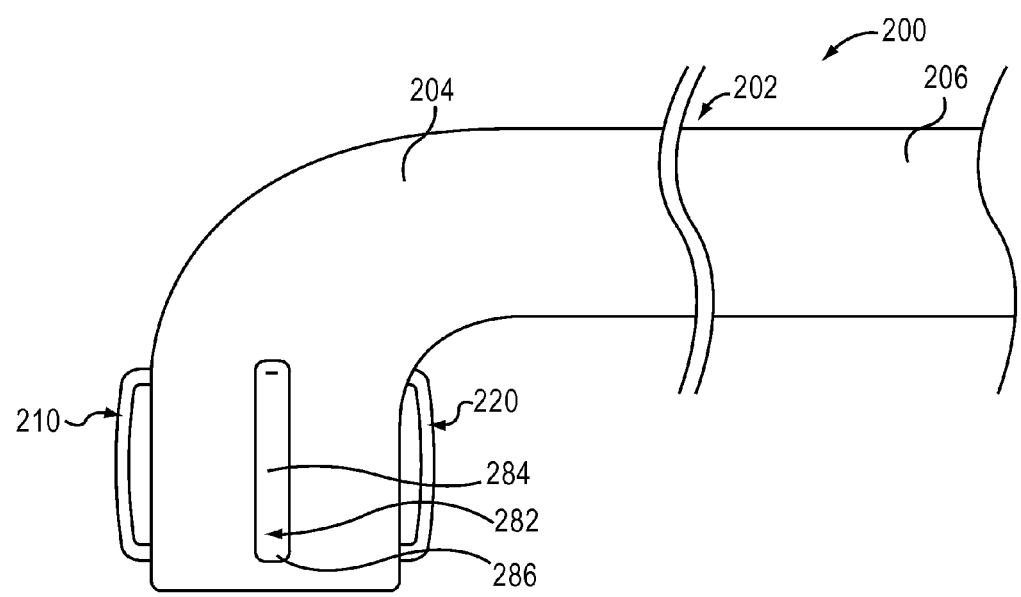

The steering components 210, 220, 280 and 282 can each be selectively actuated to maneuver and steer the distal end portion 204 of the elongate member 202 while disposed within a body lumen of a patient. More specifically, a torque can be produced at the distal end portion 204 of the elongate member 202 in response to a movement in the proximal direction by either the first or second steering components 210 and 220, causing the elongate member 202 to bend or turn, as shown in FIGS. 5 and 6. For example, the elongate member 202 can be moved between a first configuration, in which the distal end portion 204 of the elongate member 202 is substantially straight, as shown in FIG. 3, and a second configuration as shown in FIG. 5 or 6, in which the distal end portion 204 of the elongate member 202 is curved. FIG. 5 illustrates the elongate member 202 curved in a first direction, by actuating the steering component 210. FIG. 6 illustrates the elongate member 202 curved in an opposite direction by actuating steering component 220. Similarly, a torque can be produced at the distal end portion 204 of the elongate member 202 in response to a movement in the proximal direction by either the third or fourth steering components 280 and 282, causing the elongate member 202 to bend or turn. In other words, the elongate member 202 can move between the substantially straight configuration, as shown in FIG. 3, and a curved configuration similar to that shown in FIGS. 5 and 6.

In this embodiment, the first and second steering components 210 and 220 bend the elongate member 202 within a plane substantially perpendicular to a plane within which the third and fourth steering components 280 and 282 bend the elongate member 202. For example, the first and second steering components 210 and 220 can bend the elongate member 202 in an up direction and a down direction, respectively. The third and fourth steering components 280 and 282 can bend the elongate member 202 in a first lateral direction and second lateral direction, respectively. The second lateral direction is opposite to the first lateral direction. Specifically, each of the steering components 210, 220, 280 and 282 bend the elongate member 202 in a direction different from one another. A combination of the steering components 210, 220, 280 and 282 can bend the elongate member 202 in a direction different from the above mentioned directions. For example, the first steering component 210 and the third steering component 280 can collectively bend the elongate member 202 in a direction that is both in the up direction and the first lateral direction. For example, the second steering component 220 and the fourth steering component 282 can collectively bend the elongate member 202 in a direction that is both in the down direction and the second lateral direction. In some embodiments, the directions the first and second steering components bend the elongate member are not opposite. In some embodiments, the directions the third and fourth steering components bend the elongate member are not opposite.

Although in this embodiment, the distal ends 216 and 226 of the steering components 210 and 220, respectively, are coupled to the outer surface of the elongate member 202, the steering components 210 and 220 can alternatively be coupled to an inner portion of the distal end portion 204 of the elongate member 202. In some embodiments, the distal end of the third steering component 280 and the distal end 286 of the fourth steering component 282 can be coupled to an inner portion of the distal end portion 204 of the elongate member 202. In other embodiments, the distal ends of the steering components can be integrated into the distal end portion of the elongate member. In another embodiment, the steering components 210, 220, 280 and 282 can include a shape memory alloy configured to bend the distal end portion 204 of the elongate member 202 in response to a change of the load applied by the steering components 210, 220, 280 and 282.

As stated above, in this embodiment, the electrical component 208 is an imaging device 208. The endoscope 200 includes a lens 226 disposed within the lumen 225 of the distal end portion 204. A focal plane defined by the lens 226 corresponds to the position of the imaging device 208. The lens 226 can have one of a variety of different lens configurations, including for example, biconvex, plano-convex, convex-concave, meniscus, plano-concave, biconcave, etc. Each lens configuration defines, at least in part, the position of the focal plane. The lens configuration of the lens 226 also defines, at least in part, the magnification of the image produced by the endoscopic imager 208. In other embodiments, more or less than two lenses can optionally be used.

The imaging device 208 can produce an image focused by the lens 226 so that the image can be output to a processor or display monitor as described previously. The imaging device 208 can be any of a variety of different imaging devices, including for example, a charge coupled device (CCD), a complementary metal-oxide-semiconductor (CMOS) sensor, an active pixel sensor, a thermal imaging sensor, a video camera tube, a gamma camera sensor, a x-ray sensor, or the like.

The medical device 200 also includes an actuator 240 as shown in FIG. 4. The actuator 240 is coupled to a proximal end portion 212 and 222 of the steering components 210 and 220, respectively. The actuator 240 can be used to selectively pull (apply a proximal force) on the steering components 210 and 220 to maneuver and steer the distal end portion 204 of the elongate member 202. In this embodiment, the actuator 240 includes a rotatable dial 242 operatively coupled to the first steering component 210 and the second steering component 220. The rotatable dial 242 can be used to selectively move the first steering component 210 and/or the second steering component 220. For example, the rotatable dial 242 can be rotated clockwise such that the first steering component 210 is pulled proximally, and the distal end portion 204 of the elongate member 202 is moved to a curved configuration, as shown in FIG. 5. Similarly, the rotatable dial 242 can be turned counterclockwise, such that the second steering component 220 is pulled proximally, and the distal end portion 204 of the elongate member 202 is moved to a curved configuration as shown in FIG. 6. The actuator 240 is just one example of an actuator that can be used to actuate the steering components 210 and 220. In other embodiments, various other types and configurations of actuators can alternatively be used. For example, a proximal end portion of each of the steering components can extend outside of the patients body such that a user can selectively pull one of the steering components proximally. In another alternative embodiment, the rotatable dial 242 can pull the one steering component and push the other steering component or vice-versa.

In the illustrated embodiment, although the actuator 240 depicts the first and second steering components 210 and 220, it should be understood that the actuator 240 can also include the third and fourth steering components 280 and 282. In some embodiments, a second actuator having similar components is coupled to the proximal end portion of the elongate member to selectively actuate the third and fourth steering components.

FIGS. 7 and 9 are a distal end view and side view, respectively, of a medical device according to another embodiment of the invention. FIG. 8 is a cross-sectional view of the medical device taken along the line 8-8 of FIG. 7. As shown in FIG. 8, an endoscope 300 includes an elongate member 302 having a proximal end portion 306 and a distal end portion 304. The distal end portion 304 of the elongate member 302 includes a lens 326 and an electrical component 308. As with the previous embodiment, the electrical component 308 is an endoscopic imager 308. A conductive elongate component 354 is electrically coupled to the endoscopic imager 308 and can provide electrical power to or conduct a signal produced by the endoscopic imager 308 to a processor (not shown) and/or a display monitor (not shown) disposed at the proximal end portion 306 of the elongate member 302.

An elongate conductive mechanical component 350 is disposed about at least a portion of an outer surface 356 of the elongate member 302. In this embodiment, the elongate conductive mechanical component 350 includes multiple interwoven wires forming a braid-type configuration, and having a cylindrical shape. The elongate conductive mechanical component 350 (also referred to as braided wire 350) has an electrical function and a mechanical function. The braided wire 350 is electrically coupled to the endoscopic imager 308 via a connector(s) 352. A proximal end portion (not shown) of the braided wire 350 can be coupled to a visual display (not shown) and/or processor (not shown). The braided wire 350 can be used to conduct electrical power from the proximal end portion 306 of the elongate member 302 (e.g., from a power source (not shown)) to the endoscopic imager 308 to enable the endoscopic imager 308 to produce an imaging signal. The braided wire 350 can also be used to structurally support the elongate member 302 and/or other mechanical functions. For example, the braided wire 350 can provide torque strength, stiffness and puncture resistance. The braided wire 350 can also include an insulation layer (not shown) disposed about the individual wires. Alternatively, the braided wire 350 can be encased or surrounded by an insulation layer or coating (not shown). Although, in this embodiment, the braided wire 350 is disposed about at least a portion of the outer surface 356 of the elongate member 302 (e.g., separate from the elongate member 302), it should be understood that the braided wire 350 can be embedded within the elongate member 302 or disposed within an internal lumen (e.g., a working channel) defined by the elongate member 302.

In this embodiment, the braided wire 350 has interwoven wires forming a mesh or network configuration. That said, it should be understood that the elongate conductive mechanical component 350 can have other configurations while still providing structural support to the elongate member 202. For example, in some embodiments, the elongate conductive mechanical component can include multiple longitudinally extending (e.g., extending in a proximal-to-distal direction) members disposed about the outer surface of the elongate member 202 with connections between the elongate members at spaced locations along a longitudinal length of the elongate member 202.

In an alternative embodiment, the electrical functionalities of the braided wire 350 and the conductive elongate component 354 can be reversed. For example, the electrical function of the braided wire 350 can be to conduct a signal produced by the endoscopic imager 308 to the proximal end portion 306 of the elongate member 302. The electrical functionality of the conductive elongate component 354 can be to conduct electrical power from a power source at the proximal end portion 306 of the elongate member 302 to the endoscopic imager 308.

In another alternative embodiment, the braided wire 350 is a first braided wire 350. The endoscope 300 can include a second braided wire (not shown) having a cylindrical configuration and disposed about at least a portion of an outer surface of the first braided wire 350. The second braided wire can be electrically coupled to the endoscopic imager 308 and configured to conduct a signal from the endoscopic imager 308 to the proximal end portion 306 of the elongate member 302. The electrical functionality of the first braided wire 350 and the second braided wire can also be reversed.

In some embodiments, the endoscope can be shielded by the braided wire and other devices, such as, for example, the processor, the display monitor, etc., can be separately shielded to collectively shield the endoscope system. For example, the braided wire can provide electromagnetic (EM) and/or noise protection to the endoscope. A paint disposed along an interior wall of the display monitor can provide EM and/or noise protection to the display monitor. In other words, the braided wire can inhibit EM energy from entering the elongate member from outside the elongate member or from leaving the elongate member. In some embodiments, a second braided wire can be disposed within the elongate member can provide electrical power to the endoscopic imager and/or conduct a signal from the endoscopic imager.

FIGS. 10 and 11 illustrate a cross-sectional view and a side view, respectively, of a medical device according to another embodiment of the invention. As shown an FIG. 10, an endoscope 400 includes an elongate member 402 having a distal end portion 404 and a proximal end portion 406. The distal end portion 404 of the elongate member 402 can be inserted into a patient. The proximal end portion 406 of the elongate member 402 can be operatively coupled to a display monitor (not shown). As with the previous embodiment, the distal end portion 404 of the elongate member 402 includes a lens 426 and an endoscopic imager 408 that can receive optical energy and produce a signal based on the optical energy.

In this embodiment, a first elongate conductive mechanical component 410, a second elongate conductive mechanical component 420, a third elongate conductive mechanical component 480 and a fourth elongate conductive mechanical component 482 are each disposed about at least a portion of an outer surface 456 of the elongate member 402. The multiple elongate conductive mechanical components 410, 420, 480 and 482 are interwoven with one another to collectively form a braid-type configuration having a cylindrical shape. Each of the elongate conductive mechanical components 410, 420, 480 and 482 have an electrical function and a mechanical function. Collectively, the elongate conductive mechanical components 410, 420, 480 and 482 can structurally support the elongate member 402. For example, the elongate conductive mechanical components 410, 420, 480 and 482 can, collectively, provide torque strength, stiffness and puncture resistance. The elongate conductive mechanical components 410, 420, 480 and 482 are electrically coupled to the endoscopic imager 408 via connection members 411, 421, 481 and 483, respectively. The first elongate conductive mechanical component 410 and the second elongate conductive mechanical component 420 are coupled to a processor (not shown) and/or the display monitor. The third elongate conductive mechanical component 480 and the fourth elongate conductive mechanical component 482 are coupled to a power source (not shown).

As described above, the elongate conductive mechanical components 410, 420, 480 and 482 each have an electrical function. The first elongate conductive mechanical component 410 can conduct a first signal (e.g., S+) from the endoscopic imager 408 to the processor and/or the display monitor. The second elongate conductive mechanical component 420 can conduct a second signal (e.g., S−) different from the first signal from the endoscopic imager 408 to the processor and/or display monitor. The third elongate conductive mechanical component 480 can conduct a first electrical power (e.g., P+) from the power source to the endoscopic imager 408 to enable the endoscopic imager 408 to produce an imaging signal. The fourth elongate conductive mechanical component 482 can conduct a second electrical power (e.g., P−) different from the first electrical power from the power source to the endoscopic imager 408. Each of the elongate conductive mechanical components 410, 420, 480 and 482 have an insulation layer. In some embodiments, the endoscope can include more or less than four elongate conductive mechanical components.

Although, in this embodiment, the elongate conductive mechanical components 410, 420, 480 and 482 are disposed about at least a portion of the outer surface 456 of the elongate member 402 (e.g., separate from the elongate member 402), it should be understood that the elongate conductive mechanical components 410, 420, 480 and 482 can be embedded within the elongate member 402 or disposed within an internal lumen (e.g., a working channel) defined by the elongate member 402.

In some embodiments, the first elongate conductive mechanical component and the second elongate conductive mechanical component can conduct the same signal (e.g., an imaging signal based on tissue distal the elongate member) from the endoscopic imager to the processor and/or display monitor. In some embodiments, one of the elongate conductive mechanical components can conduct electrical power from the power source to the endoscopic imager. The other elongate conductive mechanical components can conduct one or more signals from the endoscopic imager to the processor and/or display monitor. In other embodiments, one of the elongate conductive mechanical components can conduct a signal from the endoscopic imager to the processor and/or display monitor. The other elongate conductive mechanical components can conduct electrical power from the power source to the endoscopic imager.

In some embodiments, the elongate conductive mechanical components provide EM or noise shielding. In some embodiments, a protective paint can be disposed along surfaces of various components (e.g., the elongate member, the display monitor) to provide EM or noise shielding.

In some embodiments, a control or feedback signal can be sent from the proximal end portion of the elongate member to the endoscopic imager via one of the elongate conductive mechanical components. The control or feedback signal can, for example, reduce the illuminating intensity of an illumination source when the detector becomes saturated due to a too bright image. For example, the detector can be a temperature sensor and the electrical function of the first elongate conductive component can be to help control temperature of tissue at or near the distal end of the elongate medical device when disposed within the patient. The amount of electrical power to produce heat can be adjusted to change the temperature of the tissue based on a control and/or feedback signal.

FIGS. 12 and 13 illustrate a medical device according to another embodiment of the invention. FIG. 12 is a distal end view of a medical device 500. FIG. 13 is a cross-sectional view of the medical device 500 taken along the line 13-13 of FIG. 12. As shown in FIG. 12, the endoscope 500 includes an elongate member 502 having a proximal end portion 506 and a distal end portion 504. The elongate member 502 defines a first lumen 566 and a second lumen 564. A first lens 526 and a second lens 528 are disposed within the first lumen 566 at the distal end portion 504 of the elongate member 502. An endoscopic imager 508 is also disposed within the lumen 566 at the distal end portion 504 of the elongate member 502, and is coupled to a conductive elongate member 554 that extends through the lumen 566 of the proximal end portion 506 of the elongate member 502. As with the previous embodiment, the conductive elongate component 554 is electrically coupled to the endoscopic imager 508 and is configured to conduct a signal produced by the endoscopic imager 508 to the proximal end portion 506 of the elongate member 502 and to, for example, a processor (not shown) and/or display monitor (not shown).

The second lumen 564 (e.g., channel) is configured to receive a medical device or tool therethrough. For example, the second lumen 564 extends between the proximal end portion 506 of the elongate member 502 and the distal end portion 504 of the elongate member 502. A medical device tool 560, such as, for example, forceps, can be slidably moved from the proximal end portion 506 of the elongate member 502 to the distal end portion 504 of the elongate member 502 to access tissue located within a body lumen at or near the distal end portion 504 of the elongate member 502. The mechanical device tool 560 can be used to perform a medical procedure such as to remove polyps from the body lumen, and can also be used to conduct an electrical signal to or from the electrical component 508. For example, a conductive connector 562 can extend through an opening 518 in a wall of the elongate member 502 to electrically couple the endoscopic imager 508 to the medical tool 560. The conductive connector 562 can engage (e.g., contact) the medical device tool 560 upon passage of the medical tool distally through the second lumen 564, as shown in FIG. 13. Thus, as the medical tool is being used to perform a medical procedure within a body lumen, it can also conduct electrical power from a power source (not shown) to the endoscopic imager 508 via the conductive connector 562. In such an embodiment, the handle of the medical tool used by the operator can be electrically insulated.

In an alternative embodiment, the electrical functionality of the medical device tool 560 and the conducive elongate component 554 can be reversed. For example, the medical device tool 560 can be used to conduct a signal from the endoscopic imager 508 to, for example, a display monitor and/or processor. The conductive elongate component 554 can be used to conduct electrical power from a power source to the endoscopic imager 508.

In some embodiments, the medical device tool 560 can also include an electrical component (not shown). The medical device tool 560 can conduct electrical power from a power source to the electrical component of the medical device tool 560. The electrical component of the medical device tool 560 can include, for example, an imager, a detector, a sensor, etc.

Figure 14:
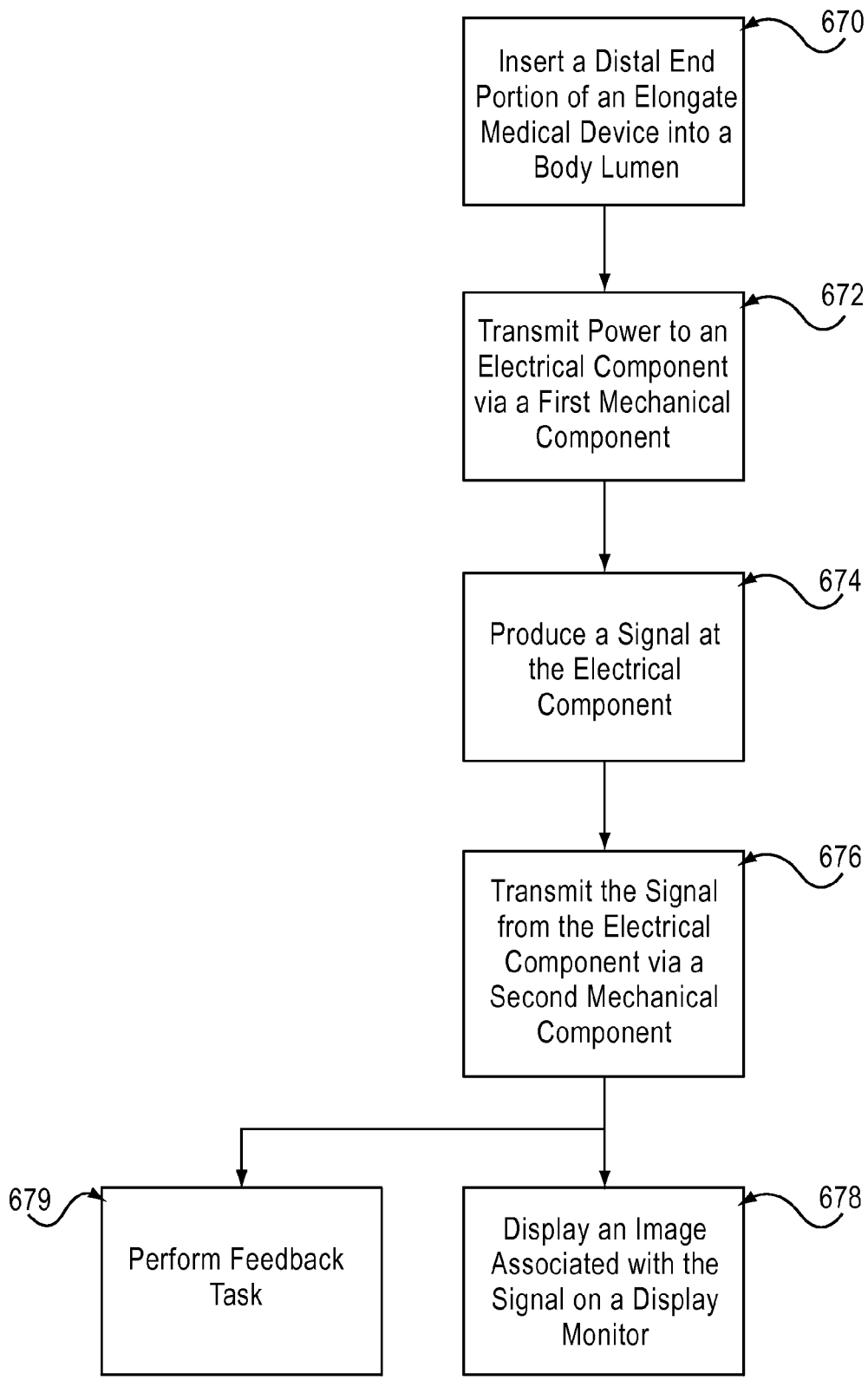
FIG. 14 is a flowchart illustrating a method of using a medical device according to an embodiment of the invention.
Figure 15:
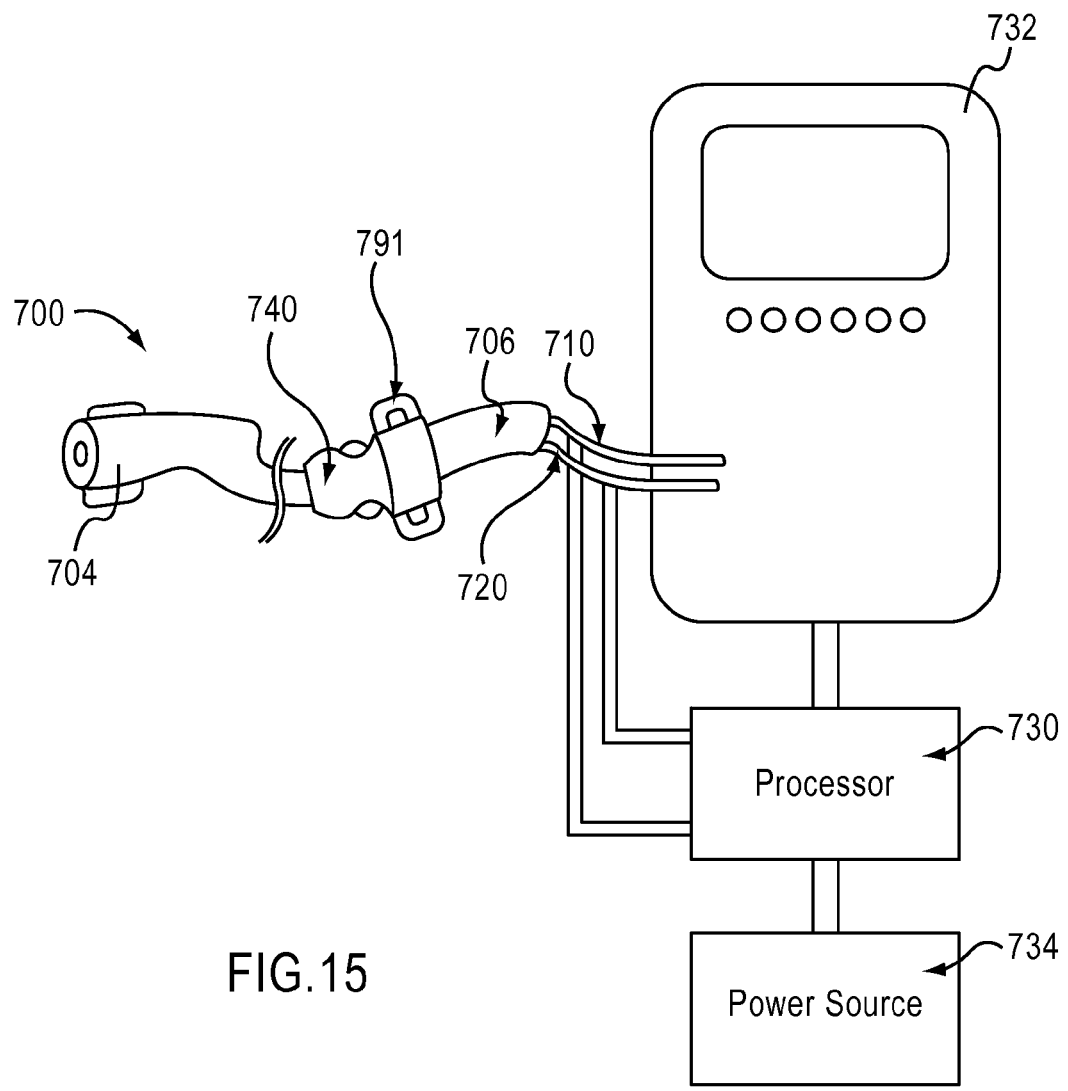
FIG. 15 is a side perspective view of a medical device shown operatively coupled to a visual display.

FIG. 14 is a flowchart illustrating a method of using an endoscope according to an embodiment of the invention. At 670, a distal end portion of an elongate medical device is inserted into a body lumen. The elongate medical device can be, for example, an embodiment of an endoscope as described herein. For example, the elongate medical device can include an electrical component disposed within a distal end portion of the elongate medical device and can include a first elongate conductive mechanical component. The first elongate conductive mechanical component can perform a mechanical function and also serve as a transmission medium for conducting electrical power to the electrical component or conducting a signal generated by the electrical component to, for example, a processor or display monitor. The elongate medical device can optionally include a second elongate conductive mechanical component that can perform a mechanical function and also be used to conduct an electrical signal to or from the electrical component. For example, in some embodiments, the distal end portion of the medical device is moved by the first elongate conductive mechanical component and/or the second elongate conductive mechanical component as described herein.

At 672, electrical power is conducted from a power source to the electrical component via, for example, the first elongate conductive mechanical component. At 674, an imaging signal is produced by the electrical component. At 676, the imaging signal is conducted from the electrical component to, for example, a processor or display monitor via the second elongate conductive mechanical component. At 678, an image associated with the imaging signal is displayed on a display monitor coupled to the medical device based on the imaging signal, a temperature signal, a pressure signal, a feedback control signal or the like. At 679, the elongate medical device can perform a feedback task as discussed above.

FIG. 14 is a side perspective view illustrating a medical device shown operatively coupled to a display monitor 732 and a processor 730. The processor 730 is coupled to the display monitor 732 and a power source 734. A first and second elongate conductive mechanical component 710 and 720 of an endoscope 700 are shown coupled to a display monitor 732 such that an image produced by an electrical component at a distal end portion 704 of the endoscope 700 can be output to the display monitor 732. Electrical power can be sent from the power source 734 to the distal end portion 704 of the endoscope 700 via at least one of the first and second elongate conductive mechanical components 710 and 720. In this embodiment, the endoscope 700 includes an actuator 740 that can selectively move the distal end portion 704 of the endoscope 700 via the first and/or second elongate conductive mechanical components 710 and 720. The endoscope 700 also includes a handle 791 coupled to the proximal end portion 706 of the endoscope 700. The handle 791 includes at least one control device, such as, for example, the actuator 740 to control and maneuver the endoscope 700.

The endoscope can be formed from any appropriate material or materials, such as, for example, biocompatible polymers (e.g., rubber), biocompatible metals, or other biocompatible materials. For example, the elongate body of the endoscope can be formed with one or more materials such as, titanium, stainless steel, or the like. A portion of the endoscope, such as, for example, the distal end portion of the endoscope can be formed of an opaque material. At least some or part of the endoscope can be a disposable device.

In one embodiment, an elongate member has a proximal end portion and a distal end portion. The distal end portion is configured to be inserted into a body lumen. An electrical component is disposed within the distal end portion of the elongate member and configured to produce a signal. An elongate conductive mechanical component has a proximal end portion and a distal end portion. The distal end portion of the elongate conductive mechanical component is electrically coupled to the electrical component and configured to conduct at least one of the signal from the electrical component to the proximal end portion of the elongate conductive mechanical component or electrical power from the proximal end portion of the elongate conductive mechanical component to the electrical component.

In some embodiments, the elongate conductive mechanical component is a first elongate conductive mechanical component. A second elongate conductive mechanical component has a proximal end portion and a distal end portion. The distal end portion of the second elongate conductive mechanical component is electrically coupled to the electrical component. The second elongate conductive mechanical component is configured to conduct at least one of the signal from the electrical component to the proximal end portion or the electrical power from the proximal end portion of the second elongate conductive mechanical component to the electrical component.

In some embodiments, the signal is a first signal. The electrical power is a first electrical power. The elongate conductive mechanical component is a first elongate conductive mechanical component. A second elongate conductive mechanical component has a proximal end portion and a distal end portion. The distal end portion of the second elongate conductive mechanical component is electrically coupled to the electrical component. The second elongate conductive mechanical component is configured to conduct at least one of a second signal from the electrical component to the proximal end portion of the second elongate conductive mechanical component or a second electrical power from the proximal end portion to the electrical component.

In some embodiments, the elongate conductive mechanical component is configured to move the elongate member from a first configuration to a second configuration. In some embodiments, the elongate conductive mechanical component is a braided wire having a cylindrical configuration and disposed about at least a portion of an outer surface of the elongate member. The elongate conductive mechanical component is configured to structurally support the elongate member.

In some embodiments, the electrical component is a first electrical component. A second electrical component is coupled to the distal end portion of the elongate member. In some embodiments, the electrical component is an endoscopic imager. In some embodiments, the proximal end portion of the elongate conductive mechanical component is coupled to a visual display.

In another embodiment, an elongate member has a proximal end portion and a distal end portion. The distal end portion is configured to be received within a body lumen. The elongate member has a first configuration and a second configuration different than the first configuration. An electrical component is electrically coupled to the distal end portion of the elongate member. A steering component is coupled to the electrical component and coupled to the distal end portion of the elongate member. The steering component is configured to conduct at least one of a signal from the electrical component to the proximal end portion of the elongate member or electrical power from the proximal end portion of the elongate member to the electrical component. The steering component is configured to move the elongate member from the first configuration to the second configuration.

In some embodiments, the elongate member has a third configuration different from the first configuration and the second configuration. The steering component is a first steering component. A second steering component is coupled to the electrical component and configured to conduct at least one of the signal from the proximal end portion of the elongate member or the electrical power from the proximal end portion of the elongate member to the electrical component. The second steering component is configured to move the elongate member from the first configuration to the third configuration.

In some embodiments, a braided wire is disposed about at least a portion of the elongate member and coupled to the electrical component. The braided wire is configured to conduct electrical power from the proximal end portion of the elongate member to the electrical component. The braided wire is configured to structurally support the elongate member. In some embodiments, the braided wire includes an insulation layer.

In some embodiments, an actuator is coupled to the steering component. The steering component has a first position and a second position different than the first position. The first position is associated with the first configuration of the elongate member. The second position is associated with the second configuration of the elongate member. The actuator is configured to move the steering component between the first position and the second position.

In some embodiments, the signal includes data associated with at least one of an endoscopic image, a physical property, a temperature or a pressure. In some embodiments, the steering component includes an insulation layer. In some embodiments, the braided wire is formed from a plurality of wires and each wire from the plurality of wires includes an insulation layer.

In yet another embodiment, a method includes inserting a distal end portion of an elongate medical device into a body lumen. The elongate medical device includes an electrical component disposed within the distal end portion of the elongate medical device and an elongate conductive mechanical component that has a proximal end portion and a distal end portion. The distal end portion of the elongate conductive mechanical component is conductively coupled to the electrical component. The method includes producing a signal at the electrical component and conducting the signal from the electrical component to the proximal end portion of the elongate conductive mechanical component.

In some embodiments, the elongate conductive mechanical component is a first elongate conductive mechanical component. The medical device includes a second elongate conductive mechanical component that has a distal end portion conductively coupled to the electrical component. The method includes conducting electrical power from a proximal end portion of the second elongate conductive mechanical component to the electrical component. In some embodiments, the method includes moving the distal end portion of the medical device using the elongate conductive mechanical component.

In some embodiments, the elongate conductive mechanical component is a first elongate conductive mechanical component. The medical device includes a second elongate conductive mechanical component that has a distal end portion coupled to the electrical component. The method includes moving the distal end portion of the medical device by at least one of the first elongate conductive mechanical component or the second elongate conductive mechanical component.

In some embodiments, the producing includes producing an imaging signal. The method includes displaying an image associated with the imaging signal on a display monitor coupled to the medical device based on the imaging signal.

While various embodiments of the invention have been described above, it should be understood that they have been presented by way of example only, and not limitation. Various changes in form and details of the embodiments can be made.

For example, the endoscopes described herein can include various combinations and/or sub-combinations of the components and/or features of the different embodiments described. The endoscopes described herein can include one or more mechanical components that also have an electrical function. In addition, an elongate conductive mechanical component as described herein can provide one or more mechanical functions and/or one or more electrical functions.

An endoscope can have a variety of different shapes and sizes, and include a different quantity of lumens, and various different features and capabilities. For example, although the specific embodiments described herein illustrate an electrical component in the form of an imaging device, other types of electrical components can alternatively be included.

What is claimed is:

1. An apparatus, comprising:
   an elongate member having a proximal end portion and a distal end portion, the distal end portion configured to be inserted into a body lumen;
   an electrical component disposed within the distal end portion of the elongate member and configured to produce a signal; and
   an elongate conductive mechanical component having a proximal end portion and a distal end portion, wherein the elongate conductive mechanical component is configured to perform an electrical function and a mechanical function, the mechanical function being different from the electrical function,
   wherein the distal end portion of the elongate conductive mechanical component is electrically coupled to the electrical component, and wherein the electrical function includes transmitting the signal from the electrical component to the proximal end portion of the elongate conductive mechanical component.

2. The apparatus of claim 1, wherein the elongate conductive mechanical component is a first elongate conductive mechanical component, the apparatus further comprising:
   a second elongate conductive mechanical component having a proximal end portion and a distal end portion, the distal end portion of the second elongate conductive mechanical component being electrically coupled to the electrical component, the second elongate conductive mechanical component being configured to transmit electrical power from the proximal end portion of the second elongate conductive mechanical component to the electrical component.

3. The apparatus of claim 1, wherein the signal is a first signal, the elongate conductive mechanical component is a first elongate conductive mechanical component, the apparatus further comprising:
   a second elongate conductive mechanical component having a proximal end portion and a distal end portion, the distal end portion of the second elongate conductive mechanical component being electrically coupled to the electrical component, the second elongate conductive mechanical component being configured to transmit a second signal from the electrical component to the proximal end portion of the second elongate conductive mechanical component.

4. The apparatus of claim 1, wherein:
   the mechanical function of the elongate conductive mechanical component includes moving the elongate member from a first configuration to a second configuration.

5. The apparatus of claim 1, wherein the elongate conductive mechanical component is a braided wire having a cylindrical configuration and disposed about at least a portion of an outer surface of the elongate member, and wherein the mechanical function of the elongate conductive mechanical component includes structurally supporting the elongate member.

6. The apparatus of claim 1, wherein the electrical component is a first electrical component, the apparatus further comprising a second electrical component coupled to the distal end portion of the elongate member.

7. The apparatus of claim 1, wherein the electrical component is an endoscopic imager.

8. The apparatus of claim 1, wherein the proximal end portion of the elongate conductive mechanical component is coupled to a visual display.

9. An apparatus, comprising:
an elongate member having a proximal end portion and a distal end portion, the distal end portion being associated with a diameter of a body lumen, the elongate member having a first configuration and a second configuration different than the first configuration;
an electrical component electrically coupled to a distal end portion of the elongate member; and
a steering component coupled to the electrical component and coupled to the distal end portion of the elongate member, the steering component configured to transmit a signal from the electrical component to the proximal end portion of the elongate member, the steering component being configured to move the elongate member from the first configuration to the second configuration.

10. The apparatus of claim 9, wherein the elongate member has a third configuration different from the first configuration and the second configuration, the steering component is a first steering component, the apparatus further comprising:
a second steering component coupled to the electrical component and configured to transmit electrical power from the proximal end portion of the elongate member to the electrical component, the second steering component configured to move the elongate member from the first configuration to the third configuration.

11. The apparatus of claim 9, further comprising:
a braided wire disposed about at least a portion of the elongate member and coupled to the electrical component, the braided wire configured to transmit electrical power from the proximal end portion of the elongate member to the electrical component, the braided wire configured to structurally support the elongate member.

12. The apparatus of claim 9, further comprising:
an actuator coupled to the steering component,
the steering component having a first position and a second position different than the first position, the first position being associated with the first configuration of the elongate member, the second position being associated with the second configuration of the elongate member,
the actuator configured to move the steering component between the first position and the second position.

13. The apparatus of claim 9, wherein the signal includes data associated with an endoscopic image.

14. The apparatus of claim 9, wherein the steering component includes an insulation layer.

15. A method, comprising:
inserting a distal end portion of an elongate medical device into a body lumen, the elongate medical device including an electrical component disposed within the distal end portion of the elongate medical device and an elongate conductive mechanical component having a proximal end portion and a distal end portion, wherein the elongate conductive mechanical component is configured to perform an electrical function and a mechanical function, the mechanical function being different from the electrical function, and wherein the distal end portion of the elongate conductive mechanical device is conductively coupled to the electrical component;
producing a signal at the electrical component; and
transmitting the signal from the electrical component to the proximal end portion of the elongate conductive mechanical component.

16. The method of claim 15, wherein the elongate conductive mechanical component is a first elongate conductive mechanical component, the medical device, further including a second elongate conductive mechanical component having a distal end portion conductively coupled to the electrical component, the method further comprising:
transmitting electrical power from a proximal end portion of the second elongate conductive mechanical component to the electrical component.

17. The method of claim 15, wherein the mechanical function of the elongate conductive mechanical component includes manipulating the elongate conductive mechanical component to move the distal end portion of the medical device.

18. The method of claim 15, wherein the elongate conductive mechanical component is a first elongate conductive mechanical component, the medical device further including a second elongate conductive mechanical component having a distal end portion coupled to the electrical component, the method further comprising:
moving the distal end portion of the medical device by manipulating at least one of the first elongate conductive mechanical component or the second elongate conductive mechanical component.

19. The method of claim 15, wherein the producing includes producing an imaging signal.

20. The method of claim 15, wherein the producing includes producing an imaging signal, the method further comprising:
displaying an image associated with the imaging signal on a display monitor coupled to the medical device based on the imaging signal.

* * * * *